United States Patent [19]

Hess et al.

[11] Patent Number: 5,207,874
[45] Date of Patent: May 4, 1993

[54] PROCESS FOR THE PURIFICATION OF GLYCIDYL (METH)ACRYLATE

[75] Inventors: Raymond Hess; Christian Lacroix, both of Forbach, France

[73] Assignee: Atochem, Paris la Defense, France

[21] Appl. No.: 717,289

[22] Filed: Jun. 20, 1991

[51] Int. Cl.⁵ .................... B01D 3/36; C07D 301/32
[52] U.S. Cl. .................................. 203/8; 203/49; 203/79; 203/80; 203/92; 203/DIG. 11; 203/DIG. 21; 549/515; 549/541
[58] Field of Search ............... 203/8, 79, 85, 80, 92, 203/93, 49, 4, DIG. 21, DIG. 11; 549/515, 202, 541

[56] References Cited

U.S. PATENT DOCUMENTS

| | | | |
|---|---|---|---|
| 2,537,981 | 1/1951 | Edwards | 549/515 |
| 2,772,296 | 11/1956 | Mueller | 549/515 |
| 3,075,999 | 1/1963 | June et al. | 549/515 |
| 3,142,686 | 7/1964 | Kreps et al. | 549/515 |
| 3,239,433 | 3/1966 | Costolow | 203/8 |
| 4,755,262 | 7/1988 | Matsunaga et al. | 203/8 |

FOREIGN PATENT DOCUMENTS

| | | | |
|---|---|---|---|
| 53-90213 | 8/1978 | Japan | 549/515 |
| 2025970 | 1/1980 | United Kingdom | 549/515 |

OTHER PUBLICATIONS

*Chemical Abstracts,* vol. 105, No. 10, 8 Sep. 1986, p. 9, Stepanova et al.
*Chemie Ingenieur Technik,* vol. 45, No. 14, 1973, pp. 942-945, Hegner et al.

*Primary Examiner*—Wilbur Bascomb, Jr.
*Attorney, Agent, or Firm*—Millen, White, Zelano & Branigan

[57] ABSTRACT

The purification by distillation of glycidyl (meth)acrylate containing light products containing epichlorohydrin and light impurities, and heavy impurities comprises: in a first stage, a distillation of the glycidyl (meth)acrylate to be purified is conducted in the presence of a first solvent, e.g., water, capable of forming a low boiling point heteroazeotrope with the light impurities and epichlorohydrin, so as to obtain a head fraction which consists essentially of a solvent-light products heteroazeotrope; and, in a second stage, the glycidyl (meth)acrylate thus freed from the light products is subjected to a distillation in the presence of a second solvent, e.g., water, capable of forming a low boiling point azeotrope with glycidyl (meth)acrylate, so as to obtain a head fraction consisting essentially of the second solvent and the required pure glycidyl (meth)acrylate, thus freed from the heavy impurities, the said solvents being present, during these two distillations, throughout the distillation zone, including the boiler.

11 Claims, 1 Drawing Sheet

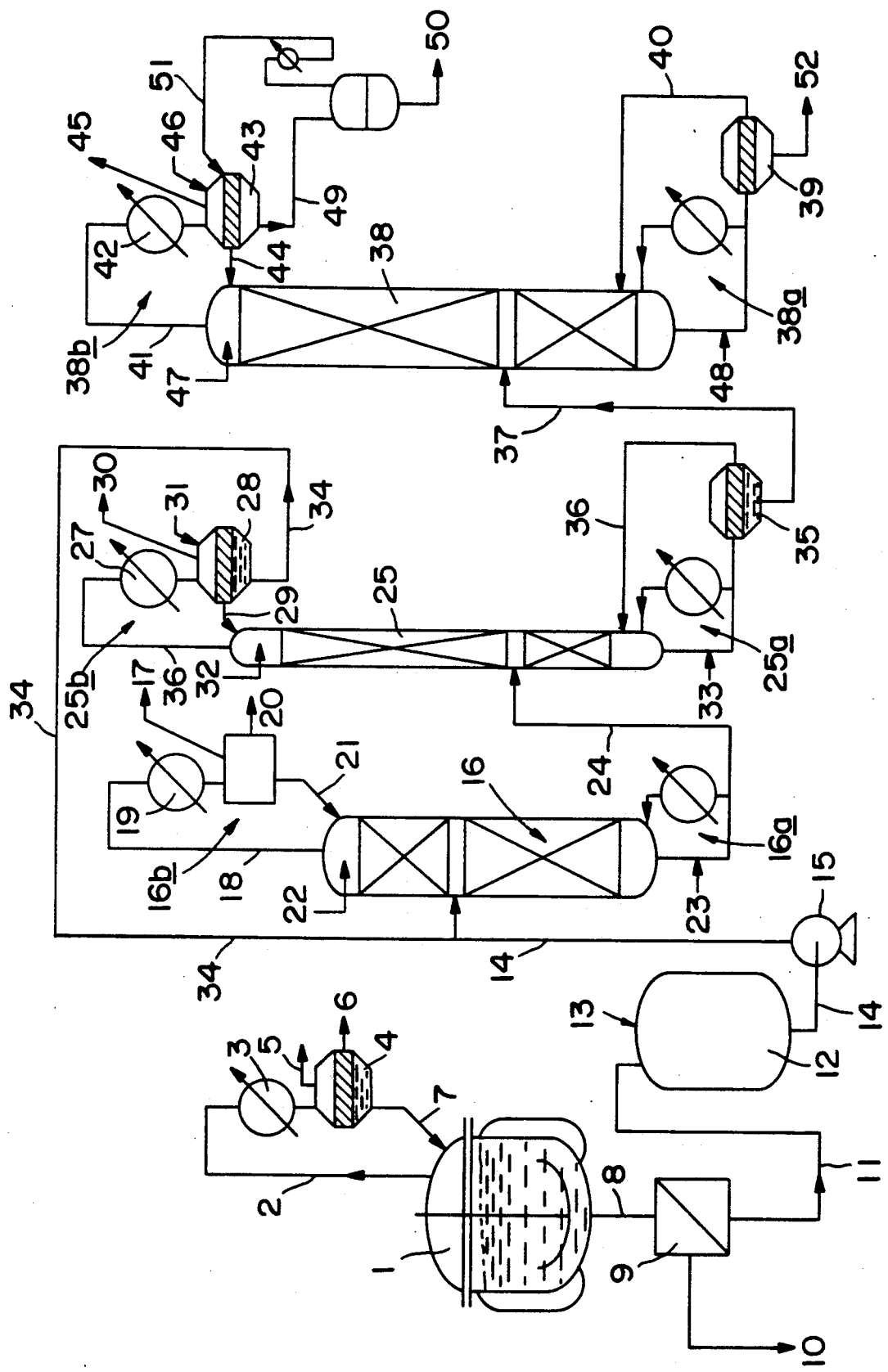

PROCESS FOR THE PURIFICATION OF GLYCIDYL (METH)ACRYLATE

BACKGROUND OF THE INVENTION

The present invention relates to a process for the purification of glycidyl methacrylate and acrylate. These compounds are known synthesis intermediates which are of particular interest because of their polymerizable acrylic double bond and their epoxy functional group.

Glycidyl methacrylate and acrylate (referred to hereinafter by the abbreviations GLYMA and GLYA) are generally obtained by the following two reaction stages, (a) neutralization of methacrylic and acrylic acids respectively with a base such as an anhydrous alkali metal carbonate or hydrogen carbonate, with epichlorohydrin as solvent, which produces the solid acid salt which remains in suspension in epichlorohydrin, with release of carbon dioxide and water, according to the reaction scheme below (using an alkali metal carbonate):

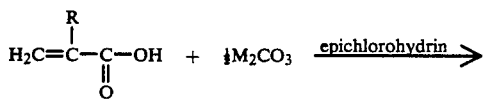

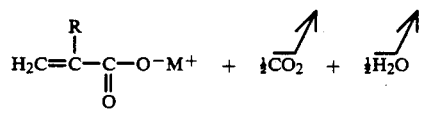

(R = H, CH$_3$) (M = alkali metal)

(R=H, CH$_3$) (N=alkali metal)

The reaction is conducted with an excess of carbonate relative to the starting acid in a reactor of the Grignard type, stirred and heated to a temperature of approximately 90°-100° C. By way of example, a reaction mixture is employed with an epichlorohydrin/carbonate/(meth)acrylic acid molar ratio of the order of 6/0.7/1 is employed. The water formed during the neutralization is removed as it is being formed, by heteroazeotropic distillation of the water-epichlorohydrin mixture, so as to avoid secondary reactions between the water and epichlorohydrin. The heteroazeotrope is condensed and is separated at room temperature, the upper aqueous phase is drawn off and the epichlorohydrin is recycled to the reactor, to obtain an acid salt remaining in suspension, in order to avoid obtaining pasty mixtures highly loaded with acid salts;

(b) the reaction of the acid salt with epichlorohydrin after introduction, as catalyst, of a quaternary ammonium salt such as trimethylbenzylammonium chloride, triethylbenzylammonium chloride, tetramethylammonium chloride and tetramethylammonium bromide, or a tertiary amine, such as triethylamine, tributylamine, triphenylamine, dimethylaniline or pyridine. The overall reaction scheme is as follows:

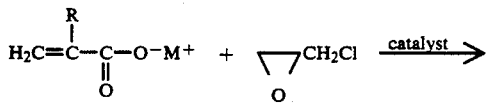

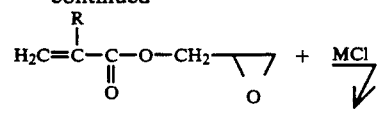

To conduct this stage, the catalyst is introduced directly into the mixture obtained in the first stage, which comprises the acid salt formed, the solvent (which is a reactant from now on) and the excess starting carbonate, the temperature being of the order of 95°-100° C. The salt MCl precipitates and GLYMA or GLYA is formed, both being liquids. The final crude reaction mixture contains solid salts in suspension, namely the excess starting sodium carbonate and the MCl formed, which are separated off, for example by filtration.

The filtered crude reaction mixture has, more particularly, the following composition:

| | |
|---|---|
| Epichlorohydrin | 70-80% by weight |
| GLYMA or GLYA | 15-25% by weight |
| Heavy impurities (which have a boiling point > that of GLY(M)A) | 2-5% by weight |
| Light impurities (which have a boiling point < that of GLY(M)A) | 1-2% by weight |

To purify the GLYMA or the GLYA, in a conventional manner, the filtered crude reaction mixture is subjected to a batchwise fractional distillation to separate off the light impurities and epichlorohydrin (topping) and then the heavy impurities (tailing).

The problem which then arises is that of the polymerization of GLYMA or GLYA, which can take place as soon as the temperature reaches at least 70° C. in the boiler. The polymerization presents the disadvantage of, on the one hand, fouling the whole apparatus, which results in a plant stoppage and, on the other hand, of resulting in a loss of product. This polymerization is related to the temperature, to the period for which this temperature has been applied, and to the addition or otherwise of at least one polymerization inhibitor. To solve this problem, the temperature can be lowered and/or the residence time in the boiler can be reduced. During the distillation the temperature rises and the pressure is reduced progressively to keep the temperature constant in the boiler. At the end of the epichlorohydrin distillation (topping) the absolute pressure is generally of the order of 1.33×10$^2$–2.66×10$^3$ Pa (1–20 mm Hg) so as not to exceed 100° C., as mentioned in DE-A-3,126,943 and FR-A-2,286,823.

Furthermore, as indicated above, at least one polymerization inhibitor is introduced into the boiler and at the head of the distillation column, such as hydroquinone, hydroquinone methyl ether or phenothiazine, which are effective in the presence of air, which is introduced continuously into the boiler.

Despite all these precautions, on the one hand, the problems of polymerization of GLYMA or GLYA in the boiler are not completely prevented and, on the other hand, the content of epichlorohydrin in the boiler after topping is still higher than or equal to 0.2%, that is to say too high.

To distil GLYMA or GLYA, by the usual technique, the absolute pressure in the boiler is of the order of 1.33×10$^2$–6.65×10$^2$ Pa (1–5 mm Hg), as indicated in the examples of German Patent Application DE-A-3,126,943. Obtaining a high vacuum is an operation which is very constraining on an industrial scale and which requires the use of a perfectly leakproof plant. Similarly, the vacuum obtained in the boiler is also limited by the pressure drops of the distillation column.

Furthermore, during the tailing of GLYMA or GLYA, the exhaustion of the heavy residue in the boiler is also limited by the risks of polymerization as soon as the temperature in the boiler reaches at least approximately 70° C.

To overcome these difficulties it is proposed, in accordance with Patent CA-A-986,126, to introduce an inert gas at the foot of the epichlorohydrin distillation column so that the remaining traces of epichlorohydrin are entrained by the inert gas. On the one hand, the introduction of such an inert gas is incompatible with the presence of a polymerization inhibitor and, on the other hand, gases contaminated by traces of epichlorohydrin, which are very difficult to purify, leave the plant. Epichlorohydrin is a toxic product whose residual contents in GLYMA or GLYA should preferably not exceed 100 ppm. Thus, the process according to Patent CA-A-986,126 would make it possible to solve the problem of residual epichlorohydrin—this being despite other difficulties, namely complicated or polluting plants—but, in no case would it solve the problem linked with the polymerization of GLYMA or GLYA.

SUMMARY OF THE INVENTION

An object of the present invention, therefore, is to provide a new process for the purification of GLYMA or GLYA involving heteroazeotropic distillations of epichlorohydrin and then of GLYMA or GLYA, which decreases the difficulties described above.

Upon further study of the specification and appended claims, further objects and advantages of this invention will become apparent to those skilled in the art.

To attain these objects, there is provided a process for the purification by distillation of glycidyl (meth)acrylate containing light impurities, light products comprising epichlorohydrin, and and heavy impurities, characterized in that:

- in a first stage, a distillation of the glycidyl (meth)acrylate to be purified is conducted in the presence of a first solvent capable of forming a low boiling point heteroazeotrope with the light impurities and epichlorohydrin, so as to obtain a head fraction which consists essentially of a solvent-light products heteroazeotrope; and
- in a second stage, the glycidyl (meth)acrylate thus freed from the light products is subjected to a distillation in the presence of a second solvent capable of forming a heteroazeotrope of low boiling point with glycidyl (meth)acrylate, so as to obtain a head fraction consisting essentially of the second solvent and the required pure glycidyl (meth)acrylate, thus freed from the heavy impurities, the said solvents being present, during these two distillations, throughout the distillation zone, including the boiler.

In accordance with a first embodiment, the process is conducted noncontinuously by removing, in a first stage, the head fraction consisting essentially of the first solvent-light products heteroazeotrope, and by then collecting glycidyl (meth)acrylate in a second stage.

In accordance with a second embodiment, the process is conducted continuously in two separate distillation columns.

The solvent capable of forming an azeotrope is preferably water in each of the distillations.

In the two embodiments (continuous or noncontinuous) a preliminary stage may be conducted to remove, by distillation under reduced pressure, a predominant part of the epichlorohydrin, at a sufficiently low temperature for no polymerization of the glycidyl (meth)acrylate to take place, for example not exceeding approximately 70° C., or else following a preferred route, continuously, a boiler with a short residence time being chosen, such as a thin-film evaporator, a scraped-film evaporator or a falling-film evaporator, in the case of which the residence times are shorter than a minute.

In accordance with this second route it is possible to operate at temperature levels of at least approximately 80° C. and capable of going up to approximately 130° C.

During the topping and tailing stages, which are carried out in the presence of water as solvent, polymerization of glycidyl (meth)acrylate is avoided, and the heavy residue is perfectly exhausted, by operating at an absolute pressure of between approximately $2.66 \times 10^3$ and $1.01 \times 10^5$ Pa (20 and 760 mm Hg), and preferably between $1.33 \times 10^4$ and $3.99 \times 10^4$ Pa (100 and 300 mm Hg), which allows the temperatures to be set between 40° and 85° C.

In addition, it is desirable that at each of the distillation stages (preliminary stage and first and second stages) at least one polymerization inhibitor should be introduced, for example of the type referred to in the preamble of this description, in a quantity equivalent to 10–1000 ppm relative to glycidyl (meth)acrylate, together with an air flow of between 0.1–10 normal liters per kilogram of glycidyl (meth)acrylate distilled.

Finally, the traces of water present in the glycidyl (meth)acrylate obtained may be vaporized in a high vacuum of $1.33 \times 10^3$ to $2.66 \times 10^3$ Pa (10 to 20 mm Hg).

The invention will be illustrated further by the following description, given with reference to the single figure of the attached drawing, showing the process operating diagram. All the percentages are given by weight, unless indicated otherwise.

The conventional reaction of synthesis of glycidyl (meth)acrylate is conducted in a stirred reactor 1 of the Grignard type, in two stages, as shown in the preamble of the description. During the first stage, as indicated, the water formed is removed by azeotropic distillation of the water-epichlorohydrin mixture. The azeotrope is therefore removed at the top via the conduit 2 and is condensed at room temperature in the condenser 3 and then separated off in the separator 4, from the upper part of which carbon dioxide is removed at 5, and in which water and epichlorohydrin are separated into an upper and lower phase respectively, the water being discharged at 6 and the epichlorohydrin being recycled at 7 into the reactor 1.

At the end of the second stage the crude reaction mixture is drained at 8 and transferred to a separating device 9, for example a filter, from which the solid salts (excess starting sodium carbonate and MCl formed) are taken out at 10, the crude reaction mixture 11, thus freed from the solid impurities, being then transferred towards a buffer tank 12, into which a stabilizer (polymerization inhibitor), for example hydroquinone, is introduced at 13.

The crude mixture stabilized in this way feeds continuously a distillation column 16 equipped with a boiler of short residence time, such as a thin-film evaporator 16a. The temperature in the boiler is preferably set at 90° C.-130° C. The distillation is carried out under a vacuum (symbolized at 170272) of the order of $1.33 \times 10^3$–$3.99 \times 10^3$ Pa absolute (10–30 mm Hg absolute), especially of approximately $2.66 \times 10^3$ Pa absolute (20 mm Hg absolute). The packed column 16 allows the epichlorohydrin following the conduit 18 to be separated off at the top 16b; it is condensed at 19 and then discharged at 20, a proportion being recycled ar 21 into the column 16. The head temperature is of the order of 20° to 40° C. In the case of these boiler temperature conditions at the operating pressure, the residual epichlorohydrin content is of the order of 0.2 to 2%. The residence time is a few seconds, and this considerably reduces any risk of polymerization of the GLYMA or GLYA in the boiler. The column 16 and the boiler are, furthermore, protected by the continuous introduction 22 of polymerization inhibitor at the top of the column and by the injection of air 23 into the boiler circuit 16a.

The stream 24 containing 0.2 to 2% by weight of residual epichlorohydrin, which is drained from the column 16 feeds an epichlorohydrin-water heteroazeotropic distillation column 25. This column 25 may be equipped with a tube boiler, in which case the residence times are of the order of 1–2 hours, or with a film (thin-film or scraped-film) evaporator, in which case the residence times may be of the order of a few seconds. In this azeotropic distillation the residence time is not critical.

The column 25 is used in combination with a vaporization circuit 25a and a head circuit 25b which comprises a conduit 26 for extracting the epichlorohydrin-water azeotrope, a condenser 27, a separator 28 and a conduit 29 for recycling water to the column 25. The latter operates under a vacuum (symbolized at 30) of $2.66 \times 10^3$ to $1.01 \times 10^5$ Pa absolute (20 to 760 mm Hg absolute), preferably of $1.33 \times 10^4$ to $3.99 \times 10^4$ Pa absolute (100 to 300 mm Hg absolute), and this fixes the boiler temperature between 40° and 85° C. The boiler temperature is, in fact, set at the boiling temperature of the azeotrope at the operating pressure. The water of formation of the azeotrope is introduced at 31 into the separator 28.

The introduction of water allows the temperature levels in the column 25 to be greatly reduced, and especially in the associated boiler, thus preventing any polymerization of the GLYMA or GLYA.

In addition, by way of precaution, a stream 32 of stabilizer is introduced into the top part of the column 25 and an air flow 33 into the vaporization circuit 25a at the foot of the column.

An epichlorohydrin-water azeotropic mixture (approximately 75% of epichlorohydrin and 25% of water) is therefore obtained at the top of the column 25 and is separated after condensing at 27. The water is recycled completely at 29 in the form of reflux, and the epichlorohydrin is drained at 34 and, if appropriate, recycled into the feed conduit 14 of the column 16.

At the foot, a crude mixture containing water is obtained, which feeds a separator 35 in which the water separates off as an upper phase. This water is recycled at 36 to the bottom part of the column 25, and the resulting topped crude mixture which has drained from the separator 35 and which contains less than 100 ppm of epichlorohydrin feeds continuously a column 38 via the circuit 37.

The column 38 is a distillation column for GLYMA or GLYA in the form of a GLYMA or GLYA-water heteroazeotrope. This column 38 operates under pressure and boiler temperature conditions which are identical with or close to those in column 25.

The boiler of the column 38 is used in combination with a separator 39 and a water recycle conduit 40, in the same way as for the column 25.

The head circuit 38b of the column 38 is precisely identical with the circuit 25b of the column 25. It comprises a pipework 41 for extracting the GLYMA or GLYA-water heteroazeotrope - which contains approximately 90% of water and 10% of GLYMA or GLYA, a condenser 42, a separator 43 and a conduit 44 for recycling water to the top part of the column 38. The application of vacuum is symbolized at 45 and the introduction of water at 46. In the same way as before, a stream of stabilizer is introduced at 47 into the top part of the column 38, and an air injection 48 is introduced into the vaporization circuit 38a.

At the head of the column 38, after condensation, separation and total reflux of the water, GLYMA or GLYA which contains traces of water at a level of 2% is drained at 49. This GLYMA or this GLYA is dried under a high vacuum, and this makes it possible to collect at 50 GLYMA or GLYA containing approximately 0.1% of water, the resulting water being recycled into the separator 43 via the conduit 51.

At the foot of column 38 a heavy residue containing less than 10of GLYMA or GLYA is drained at 52.

TABLE

Comparison of the boiling temperatures of epichlorohydrin, GLYMA, epichlorohydrin-water and GLYMA-water heteroazeotropes, of the heavy residue containing 10% of GLYMA and of the heavy residue-water containing 10% of GLYMA.

| | | Boiling temperatures (°C.) | | | | | |
|---|---|---|---|---|---|---|---|
| Pressure in Pa | (mm Hg absolute) | Epichlorohydrin | Epichlorohydrin-water | GLYMA | Heavy residue cont. 10% of GLYMA | Heavy residue-water | GLYMA-water |
| $6.65 \times 10^2$ | (5) | — | — | 62 | 120° C. | — | — |
| $2.66 \times 10^3$ | (20) | 28 | 10 | 90 | 140° C. | 26 | 20 |
| $1.33 \times 10^4$ | (100) | 62 | 38 | 126 | — | 52 | 46 |
| $1.99 \times 10^4$ | (150) | 72 | 46 | — | — | 62 | 56 |
| $2.66 \times 10^4$ | (200) | — | 54 | — | — | 70 | 64 |
| $3.99 \times 10^4$ | (300) | 90 | 64 | 155 | — | 80 | 74 |

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, as well as corresponding French application 8917135, filed Dec. 22, 1989, are hereby incorporated by reference.

EXAMPLE 1 (COMPARATIVE): Noncontinuous fractional distillation

The initial feed consists of 616 g of a crude mixture such as that drained at 11 in the FIGURE, which has the following composition:

| epichlorohydrin | 76% |
|---|---|
| GLYMA | 20.9% |
| heavies | 3% |
| total impurities | 1% |

A topping operation is conducted at an absolute pressure of $1.06 \times 10^4$ Pa (80 mm Hg) initially and $5.32 \times 10^2$ Pa (4 mm Hg) at the end of operation, the boiler temperature being approximately 80° C.

A distillation of GLYMA is then conducted at an absolute pressure of $3.99 \times 10^2$–$5.32 \times 10^2$ Pa (3–4 mm Hg), in the case of a boiler temperature lower than or equal to 100° C.

The results of the analysis of the distilled GLYMA (90 g) are as follows:

| epichlorohydrin | 0.2% |
|---|---|
| GLYMA | 98.4% |
| heavies | 0.5% |
| others | 0.9% |

The results of the analysis of the residue (26 g) are as follows:

| GLYMA | 28% |
|---|---|
| heavies | 70% |

The presence of solid GLYMA polymers as soon as the boiler temperature reaches 100° C., a high content of epichlorohydrin in the GLYMA (of the order of 2000 ppm) and a high content of GLYMA in the residue are noted.

EXAMPLE 2: Continuous distillation in three stages (including two azeotropic distillations)

An apparatus of the type of that which has just been described with reference to the single FIGURE is employed.

The feed rate of crude GLYMA is 460 g/h. This GLYMA has the following composition:

| epichlorohydrin | 79.5% |
|---|---|
| GLYMA | 17.3% |
| heavies | 3.2% |

The column 16 is subjected to the following operating conditions:

pressure: $2.66 \times 10^3$ Pa absolute (20 mm Hg absolute)
head temperature: 30° C.
boiler temperature: 110° C.

The flow rate of the head fraction, which contains 99.8% of epichlorohydrin, is 359 g/h.

The column 25 is subjected, in the presence of water, to the following operating conditions:
pressure: $1.99 \times 10^4$ Pa absolute (150 mm Hg absolute)
head temperature: 50° C.
boiler temperature: 60° C.

The flow rate of the head fraction, after separation, is 19.2 g/h. This fraction has the following composition:

| epichlorohydrin | 14% |
|---|---|
| GLYMA | 83% |
| heavies | 3% |

The column 38 is subjected, in the presence of water, to the following operating conditions:
pressure: $1.99 \times 10^4$ Pa absolute (150 mm Hg absolute)
head temperature: 52° C.
boiler temperature: 62° C.

The flow rates of the distilled head fraction after drying and of the residue are 61.4 g/h and 19.3 g/h respectively.

This distilled head fraction after drying has the following composition:

| epichlorohydrin | <100 ppm |
|---|---|
| GLYMA | >99.0% |
| heavies | <1% |

The residue has the following composition:

| epichlorohydrin | 0% |
|---|---|
| GLYMA | 10% |
| heavies | 90% |

No trace of solid polymers was noted in the plant.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for purification by distillation of glycidyl acrylate or methacrylate containing light products comprising epichlorohydrin and light impurities, and heavy impurities in a distillation zone comprising at least one column and at least one boiler, comprising:
   in a first stage, a distillation of the glycidyl acrylate and methacrylate to be purified is conducted in the presence of a first solvent capable of forming a low boiling point heteroazeotrope with the light impurities and epichlorohydrin, so as to obtain a head fraction which consists essentially of a first solvent-light products heteroazeotrope;
   in a second stage, the glycidyl acrylate or methacrylate thus freed from the light products is subjected to a distillation in the presence of a second solvent capable of forming a low boiling point heteroazeotrope with glycidyl acrylate or methacrylate, so as to obtain a head fraction consisting essentially of the second solvent and glycidyl acrylate or methacrylate thus freed from the heavy impurities, said solvents being present, during these two distillations, throughout the distillation zone, including the boiler, and in a third stage, separating the second solvent from said glycidyl acrylate or methacrylate freed from the heavy impurities.

2. A process according to claim 1, wherein said process is conducted noncontinuously by removing, in a first stage, the head fraction consisting essentially of the first solvent-light products heteroazeotrope, and by then subjecting the remaining fraction containing glycidyl acrylate or methacrylate to said second and third stages.

3. A process according to claim 1, wherein said process is conducted continuously in two separate distillation columns.

4. A process according to claim 1, wherein the solvent capable of forming an azeotrope is water in each of the distillations.

5. A process according to claim 1, wherein a preliminary stage is conducted to remove, by distillation under reduced pressure, a predominant part of the epichlorohydrin at a sufficiently low temperature for no polymerization of the glycidyl acrylate or methacrylate to take place.

6. A process according to claim 1, wherein a preliminary stage is conducted to remove a predominant part of the epichlorohydrin continuously by distillation under reduced pressure, with a short residence time in the boiler.

7. A process according to claim 6, wherein the preliminary stage is conducted at temperature levels of at least 80° C. and up to 130° C.

8. A process according to claim 1, wherein in the first and second stages, the operation is carried out at an absolute pressure of between $2.66 \times 10^3$ and $1.01 \times 10^5$ Pa (20 and 760 mm Hg) which allows the temperatures to be set between 40° and 85° C.

9. A process according to claim 1, wherein at least one polymerization inhibitor, in a quantity equivalent to 10–1000 ppm relative to glycidyl (meth) acrylate, and an air flow of between 0.1–10 normal liters per kilogram of glycidyl acrylate or methacrylate distilled are introduced at each of the distillation stages.

10. A process according to claim 4, wherein traces of water present in the resultant glycidyl acrylate or methacrylate from said third stage are vaporized under a high vacuum.

11. A process according to claim 8, wherein the absolute pressure is between $1.33 \times 10^4$ and $3.99 \times 10^4$ Pa.

* * * * *